United States Patent [19]

Idsund

[11] Patent Number: 5,002,323
[45] Date of Patent: Mar. 26, 1991

[54] TWEEZER FOR TICK REMOVAL

[75] Inventor: Ake Idsund, Stockholm, Sweden

[73] Assignee: Instruments of Sweden, Inc., Stamford, Conn.

[21] Appl. No.: 445,179

[22] Filed: Dec. 4, 1989

[30] Foreign Application Priority Data

Jun. 22, 1989 [SE] Sweden .............................. 8902272

[51] Int. Cl.$^5$ .............................................. A01M 3/00
[52] U.S. Cl. ...................................... 294/100; 606/210
[58] Field of Search .................. 294/100, 99.2; 606/210

[56] References Cited

U.S. PATENT DOCUMENTS

| | | | |
|---|---|---|---|
| 1,443,086 | 1/1923 | Muchow | 294/99.2 |
| 2,116,651 | 5/1938 | Ackerson | 294/100 X |
| 2,584,547 | 2/1952 | Cahn | 294/99.2 X |
| 4,213,460 | 7/1980 | Weiner | . |
| 4,303,268 | 12/1981 | Davidson | . |
| 4,442,837 | 4/1984 | Keatley | . |

FOREIGN PATENT DOCUMENTS

| | | | |
|---|---|---|---|
| 378116 | 6/1985 | Austria | . |
| 45424 | 4/1989 | Sweden | . |
| 993264 | 5/1965 | United Kingdom | 294/99.2 |

OTHER PUBLICATIONS

Swedish publication, Expressen, "The Party is Over for the Tick", Aug. 11, 1988.

Primary Examiner—Margaret A. Focarino
Assistant Examiner—Dean J. Kramer
Attorney, Agent, or Firm—Bryan, Cave, McPheeters & McRoberts

[57] ABSTRACT

A tweezer for removal of ticks has two legs (10, 12), connected at one end (11) by a loop formed spring, pinched together partly within a movable cylinder (26), which through the action of a coil spring (24) is pushed against the bent portions of the legs' (10, 12) end parts in order to exert a preset squeezing force between the end parts and their sharp edged gripping points (19). By retracting the cylinder (26) the gripping points (19) are opened and when the cylinder (26) is released, the legs' (10, 12) end portions and their gripping points (19) can grasp the tick (40) and its head (38) with such a predetermined force that the tweezer will lose its grip if the tick's head (38) has not first been loosened by turning. The turning is brought about by turning the cylinder (26), which maintains the predetermined pinching force by the help of the coil spring (24).

8 Claims, 6 Drawing Sheets

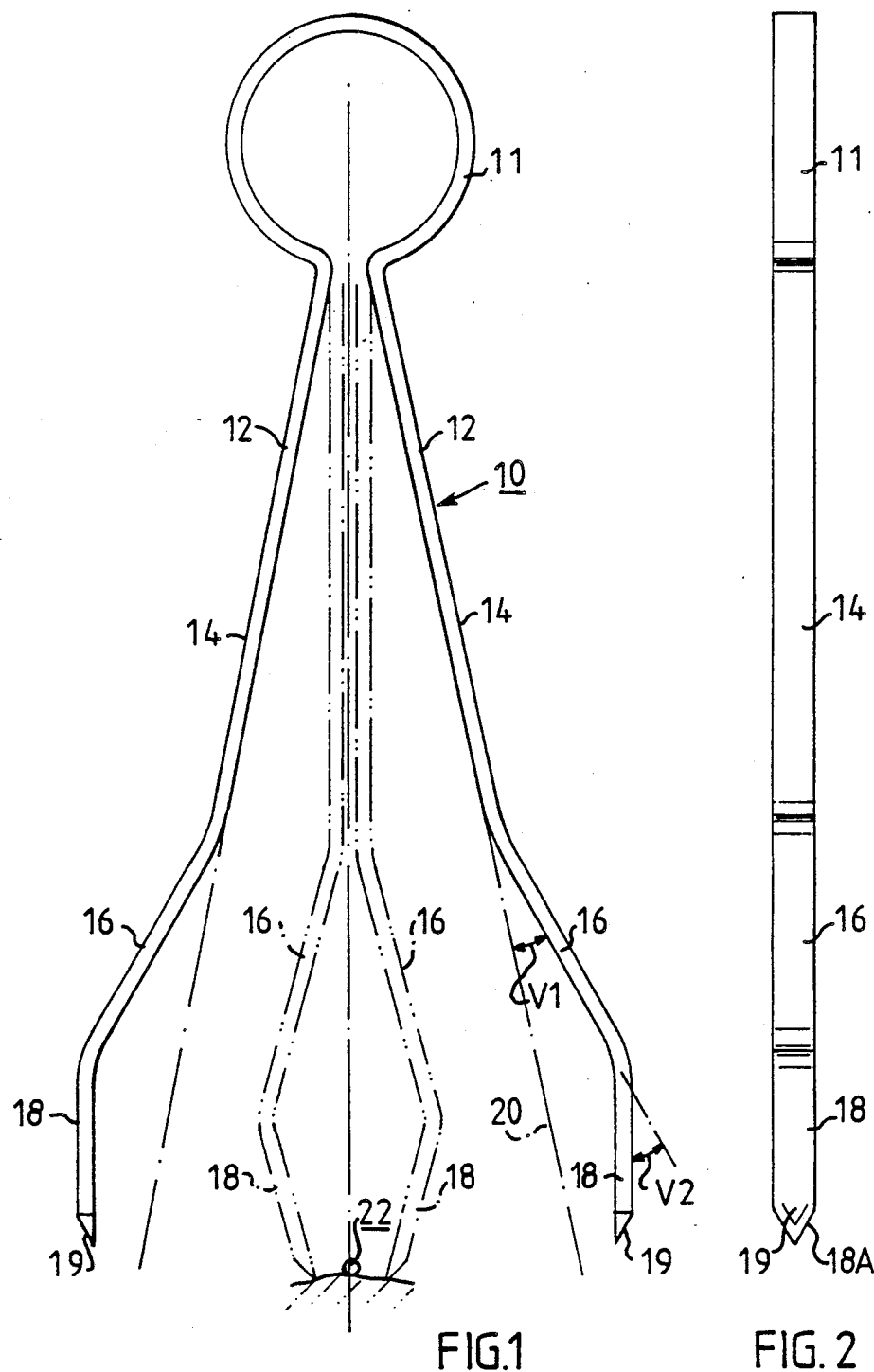

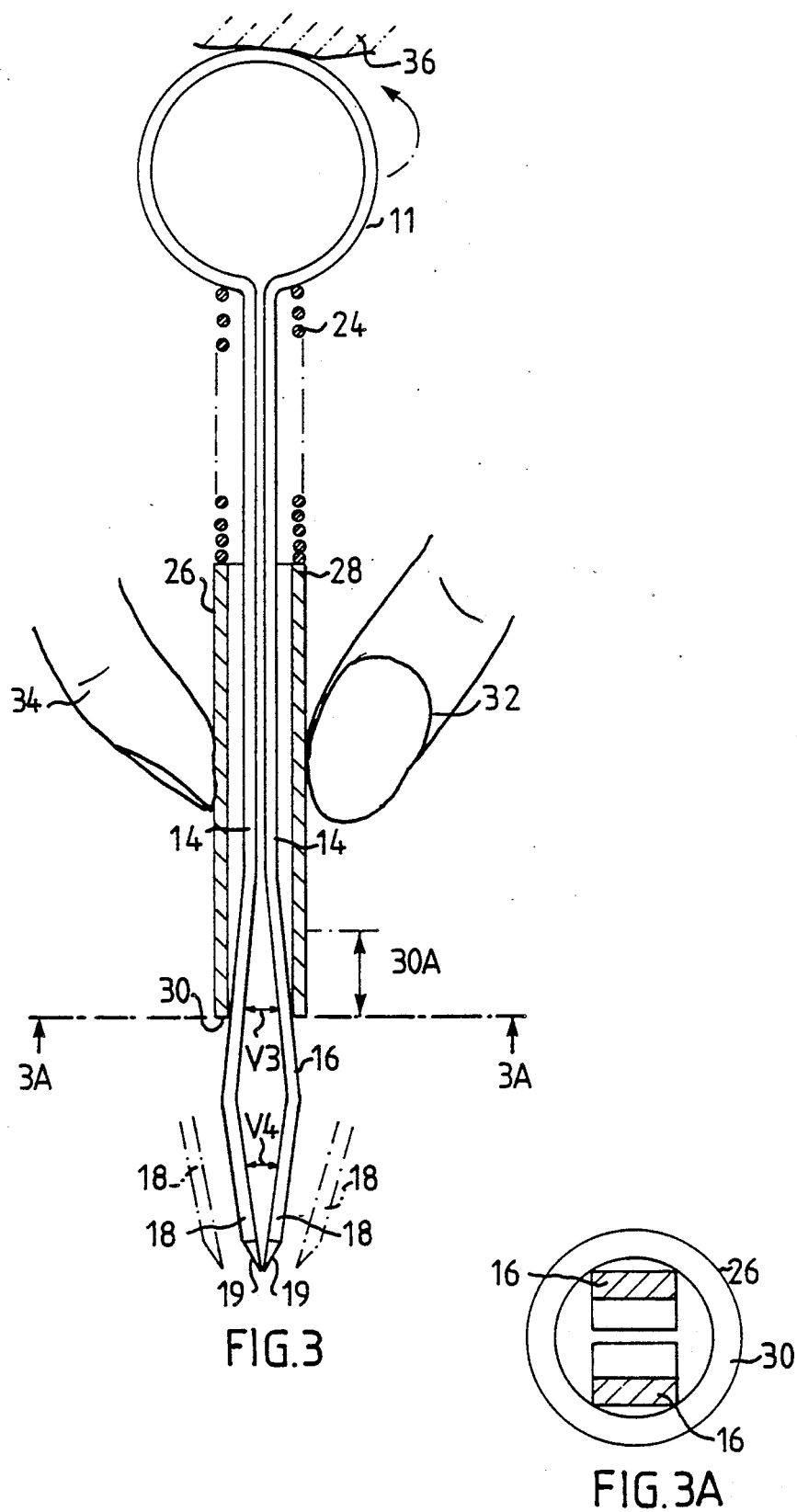

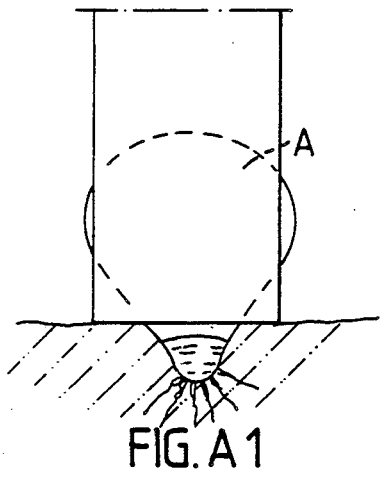
FIG. A1
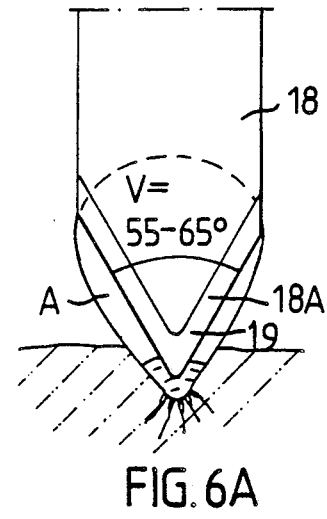
FIG. 6A
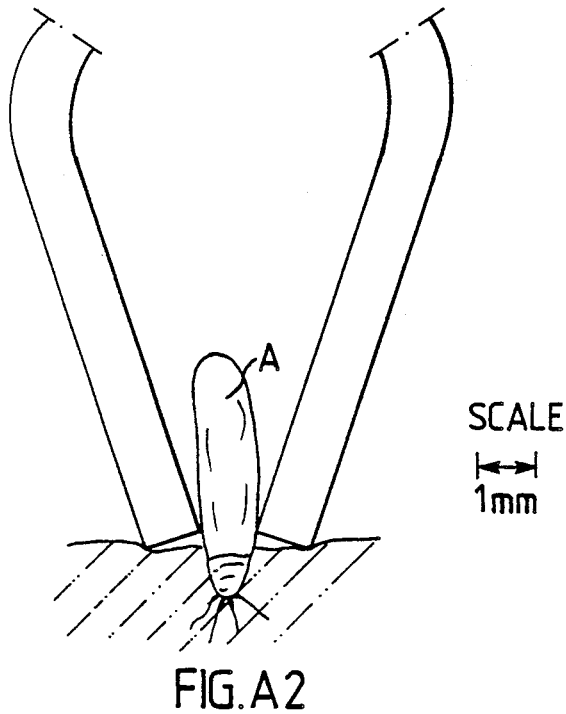
FIG. A2
SCALE
|←→|
1mm
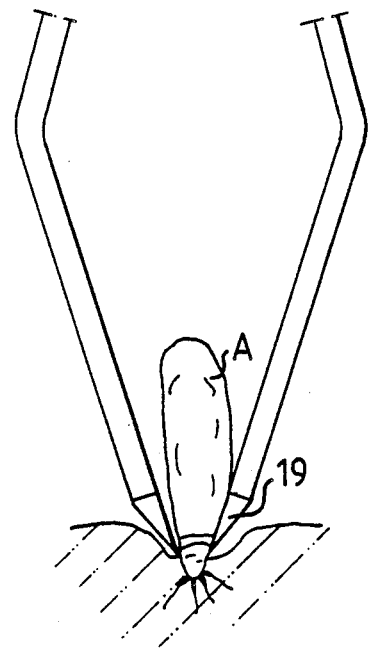
FIG. 6B

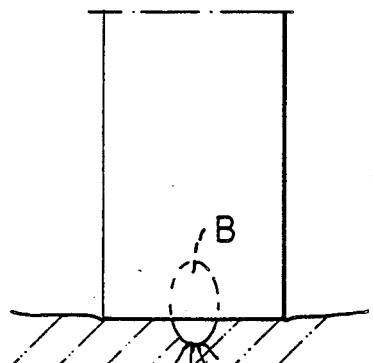
FIG. B1
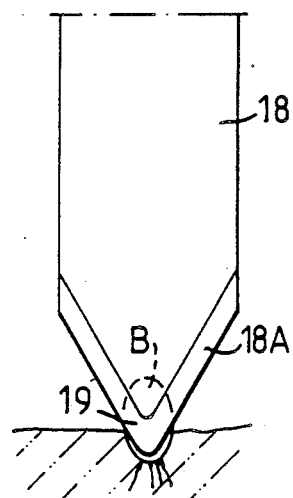
FIG. 7A
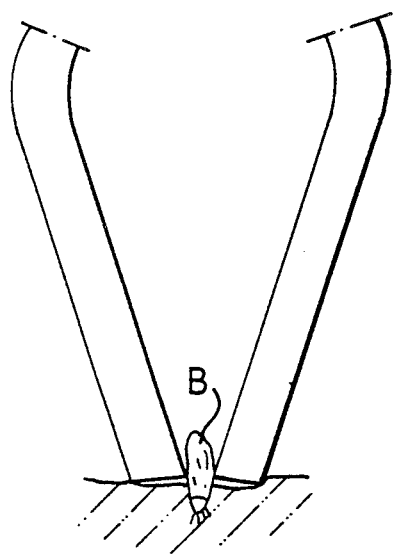
FIG. B2
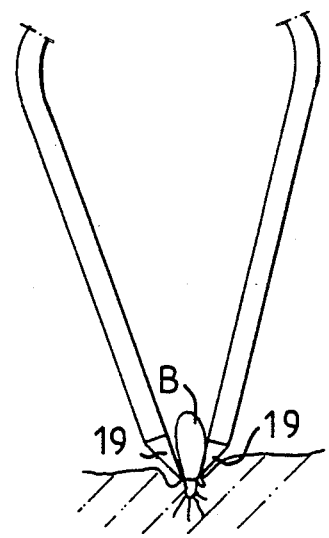
FIG. 7B

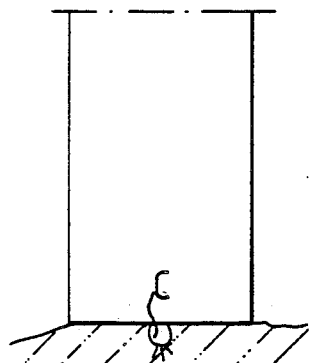
FIG.C1
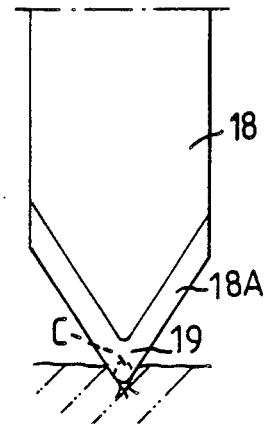
FIG.8A
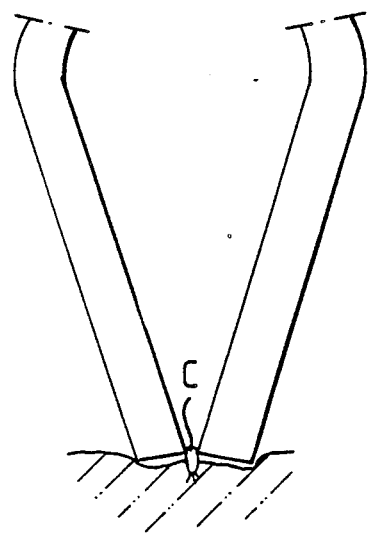
FIG.C2
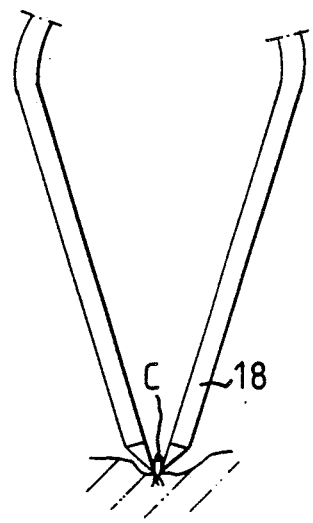
FIG.8B

TWEEZER FOR TICK REMOVAL

TECHNICAL FIELD

The present invention relates to tweezers for removing ticks from the skin of humans and animals, and more particularly to such tweezers capable of adjusting the grip on the tick's body and head to facilitate removal of the embedded tick's head from the skin.

BACKGROUND ART

Ordinary tweezers are usually not suitable for removing ticks who have embedded themselves into and fixed themselves in the skin of humans or animals. The tick has a mouth which it uses for burrowing its head into the skin. The head is only a few tenths of a millimeter in diameter and is usually relatively rigidly attached to the skin.

The body of the tick is bigger than the head and is the visible part which one can readily grasp with a tweezer or with one's fingers. However, if one tries to pull the tick by merely grasping the body in an effort to remove the tick from the skin, there is a considerable risk that the body will separate from the head of the tick, thus leaving the head in the skin which can cause serious infection, and disease. That risk can be minimized considerably by first turning the tick counter clockwise. With the fingers or with an ordinary tweezer one can, with the same grasp, only rotate a fraction of a turn, which more often than not is insufficient for the tick's head to release its grip. Moreover, if at the end of such a turn one pulls, a great risk still remains that the tick's body will be torn off from the head, which, once again, remains embedded in the skin. In order to be sure to remove the head from the skin as well, one has to rotate the tick's head three to five times around its longitudinal axis. That is, however, impossible to do with the fingers or with an ordinary tweezer without changing the grasp on the tick's head, which then unfortunately, rotates itself back into its original position, with the same inherent problems still remaining. Moreover, if a conventional or ordinary tweezer is employed to accomplish this, the ordinary tweezer still has the disadvantage that the squeezing force can only be regulated in a relatively crude fashion by squeezing the tweezer's legs together with the fingers. The squeezing force can, in that case, be too large, which means that the tweezer will not let go of the tick's body if the head is still too firmly attached to the skin when the pulling is done, once again resulting in the great risk that the tick body will be torn off the head causing considerable further difficulties in grasping the head still embedded in the skin. With these problems in mind, there have been various unsuccessful prior art attempts to provide a satisfactory tweezer type device for removing ticks, such as disclosed, by way of example, in U.S. Pat. Nos. 4,303,268; 4,442,837; and 4,213,460. However, none of these prior art devices has a satisfactory configuration which permits relative ease of reaching a tick's head remaining in the skin while enabling the tick and its head to be grasped with such a predetermined force that the tweezer will lose its grip if the tick's head has not first been loosened by turning. The problems of the prior art are even more acute in humans since ticks usually sit firmer in humans than in animals, and, thus, removal of ticks from humans provides an even greater risk that the head or parts of the tick will remain after tearing off the body with increased risks of infectious disease.

These disadvantages of the prior art are overcome by the present invention which provides a tweezer configuration which makes it possible to avoid the above described difficulties so that one, in a successful manner, can readily remove ticks embedded in the skin of both humans and animals.

DISCLOSURE OF THE INVENTION

A tweezer for removal of ticks is provided which has two legs, connected at one end by a loop formed spring, pinched together partly within a movable cylinder which, through the action of a coil spring, is pushed against the bent portions of the legs' end parts in order to exert a preset squeezing force between the end parts and their sharp edged gripping points. By retracting the cylinder the gripping points are opened and when the cylinder is released the legs' end portions and their gripping points can grasp the tick and its head with such a predetermined force that the tweezer will lose its grip if the tick's head has not first been loosened by turning. The gripping parts have such an angle between them and are touching with just enough pinching force so that they release their grip if one tries to pull the tick without having turned the head first. The turning is brought about by turning the cylinder, which maintains the predetermined pinching force by the help of the coil spring.

The tweezer's cylinder is grasped by the thumb and index finger at the same time as its loop is pushed against the palm of the same hand. With this grasp the cylinder can be pulled back a certain distance, such as around five millimeters, which leads to the gripping parts being separated about the same distance, which means that they can be positioned on either side of the tick's body. If one then releases the cylinder, the coil spring pushes the cylinder's distal edge distally, which then squeezes the legs' squeezing parts together so far that the gripping parts are squeezed firmly against the tick's body with a predetermined force which gives a sufficient amount of friction for rotating the tick's body and head when one carefully rotates the cylinder between the fingers. One can then turn the cylinder the desired number of times, such as three to five, since one can change one's grasp around the cylinder without that change influencing the tweezer's grip on the tick's head. The grip is maintained by the coil spring. Normally the tick's head will have let go of the skin after a certain number of turns, but should one not have turned a sufficient number of times and should the head then still be firmly embedded when one pulls, the squeezing force between the gripping parts and the angle between them are adjusted so that the squeezing parts are arching outwards and the gripping parts will lose their grasp by gliding off the tick's firmly attached body without its being torn off the head.

BRIEF DESCRIPTION OF DRAWINGS

FIG. 1 is a front elevation, partially diagrammatic, of the tweezer legs in open position (solid lines) and a median position (dotted line), with the gripping points still at a certain distance from each other before the final closing of the gripping points takes place;

FIG. 2 is a side elevation of the tweezer of FIG. 1, illustrating the legs being constructed from one piece of metal;

FIG. 3 is a diagrammatic illustration of the tweezer of FIG. 1, showing a longitudinal section of the tweezer with its coil spring and cylinder and with the gripping points together and the gripping parts partially abducted after the cylinder has been retracted (broken lines);

FIG. 3A is a transverse section along the line 3A—3A in FIG. 3;

BEST MODE FOR CARRYING OUT THE INVENTION

Figure 4:
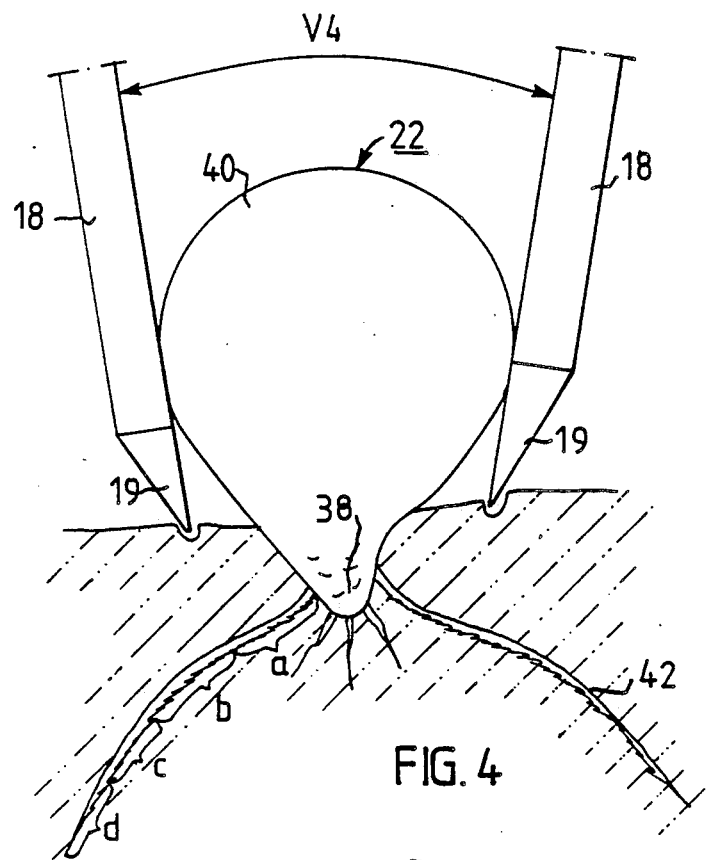
FIG. 4 is a diagrammatic illustration showing, in magnification, a tick's head embedded in the skin and its body grasped by the tweezer's gripping parts.

As is shown and preferred in FIGS. 1. and 2. an elastic piece of metal is bent into a loop with two springy legs (10 and 12) which are united through an oval or circular end (11) which can rest against the palm of the hand and be turned in a comfortable manner. Since the legs (10, 12) are preferably identical, only leg 10 will be described in the following. The leg 10 is bent into three distinct parts, namely a straight main part 14, a relatively straight squeezing part 16 and a relatively straight gripping part 18 which ends in a gripping point 19 which is flat on the inside out to the edges and which is then cut obliquely into a point with sharp edges. The angle V1 between the main part and the squeezing part 16 is, preferably, around 10–15 degrees, and the angle V2 between the squeezing part 16 and the gripping part 18 is preferably between 25 and 35 degrees. As one can see in FIG. 1, the gripping points 19 are at a distance from the line 20 which is the extension of the main part 14 which means that the gripping points 19 will be at a distance from each other when the main parts 14 are brought together (dotted lines). In order to bring the gripping points 19 together, a squeezing force must be applied to the squeezing parts 16 for the gripping parts 18 to grasp the body of the tick 22 in FIG. 1. As shown and preferred in FIG. 3, the tweezer has both the elastic legs 10 and 12 depicted in FIG. 1 and over them a coil spring 24 and a movable cylinder 26. The spring 24 is set between the end part 11 and the cylinder's 26 proximal end 28, while the cylinder's 26 distal end 30, according to FIG. 3. and 3A., has slid up on the squeezing parts 16 under counter tension of these until the gripping points 19 touch each other with a preset force determined by the spring's 24 tension, the elastic tension of the main parts 14, which are symmetrical to each other, the angle V3 between the symmetrical squeezing parts 16 and the friction between the edges of the squeezing parts 16 and the cylinder's 26 distal edge. The angle V4 between the gripping parts 18 in FIG. 3. is preferably between 10 and 20 degrees when the cylinder 26 squeezes them together as shown in FIG. 3.

A slight pulling back of the cylinder 26 preferably makes its edge slide down along the gripping parts 18 and permits them to spring out (shown with dotted lines). If the grip on the cylinder 26 is released, it will be pushed distally by the coil spring 24 to the illustrated end position pushing the gripping parts 18 together against the elasticity of the squeezing parts 16. If the main parts 14 were to extend straight directly into the gripping parts 18 instead of via the bent out squeezing parts 16 shown and preferred M FIG. 3, the cylinder 26 would have to be retracted a longer distance in order to produce the same opening of the gripping parts 18, while the friction between the main parts 14 and the end of the cylinder 26 would be greater and, thus, offer greater resistance against displacement of the cylinder 26 from its distal end position. As is shown and preferred in FIG. 3. the cylinder 26 is grasped between the thumb and the index finger 34 while the end part 11 is pushed against the palm of the hand 36. One can now easily retract the cylinder 26 a small distance in order to open the gripping parts 18 and then release the cylinder 26 so that the gripping parts 18 automatically return to their squeezing position to pinch the tick's body. Thereafter the cylinder 26 and the legs 10, 12, can be turned counter clockwise a desired number of turns to twist loose the tick's head, whereafter the tick is loose and can be pulled off the skin.

In FIG. 4. a tick embedded in the skin is illustrated, with the tick shown magnified, its head 38 furnished with a number of jaws, and its body 40. A number of barbed arms 42 which have embedded themselves in the skin are illustrated as extending from the head 38. The head 38 is also embedded in the skin in the illustration of FIG. 4. The body 40 is grasped with the gripping parts 18, which have such an angle between them and are touching with just enough pinching force so that they release their grip if one tries to pull the tick without having turned the head 38 first. By turning the tweezer, the arms 42 will be wrapped around the head 38. At the same time, the jaws will let go and after the last turn the tick's grip has been released.

Figure 5:
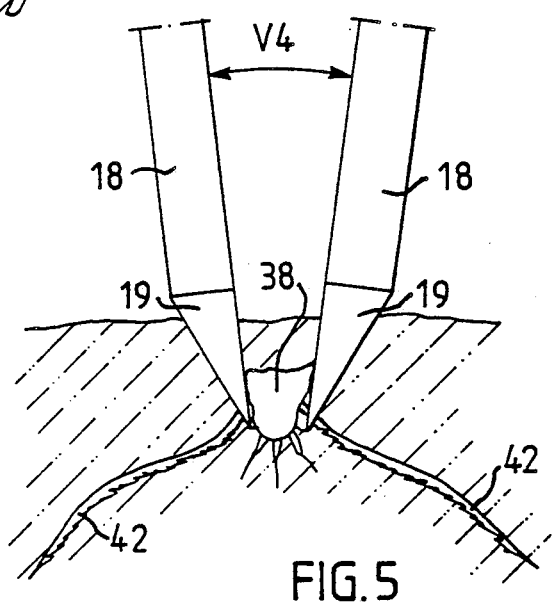
FIG. 5 is a diagrammatic illustration, similar to FIG. 4, with the tick's body torn away and the gripping points having been pushed into the skin on either side of the head in order to be squeezed together around the head before it can be rotated loose.

In FIG. 5, an illustration is shown of a situation in which the body 40 has torn off from the head 38 after an improper handling of the tweezer or after somebody has tried to initially pry the tick loose with the fingers. The tick's head 38 is not easily accessible in the skin but can relatively easily be grasped by the gripping points 19, whereafter the tweezer is turned carefully by rotating the cylinder 26. The tweezer is, in this case, a simple and effective surgical instrument. Since the gripping points 19 are preferably cut to a relatively thin knife-like point, they can in addition be used as a knife to cut the skin around a tick's head 38 to make it more easily visible and accessible.

Summarizing the above discussion, the preferred tweezer for removal of ticks which have entered into the skin, consists of two flat spring-like legs, 10, 12, which at one end, merge into each other and which at their free ends have gripping points 19 which can be brought together against the spring like action, with the legs (10, 12) being formed with a longer straight part (14) which originates from the end part (11) and which at its end is formed into an abducted relatively straight squeeze part (16) which preferably forms an angle (V1) 15 to 25 degrees with the main part and which in turn merges with a straight adducted gripping part (18) which preferably forms an angle (V2) 25 to 35 degrees with the gripping part (18) and which at its free end is formed into a gripping point (19) which is flat on the inside and obliquely cut into a double edged relatively thin knife-like point in order to reach a tick head 38 remaining in the skin. In the leg's free position their respective points are at a distance from a line (20) which comprises an extension of the straight main parts (14) inside so that after bringing the straight main parts (14) together the squeeze parts (16) must be subject to a certain force to bring the gripping points (19) together.

The coil spring (24) and the movable cylinder (26) are applied over the legs (10, 12) so that the spring (24) is under tension between the cylinder's proximal end (28) and the legs' proximal ends (11) and the cylinder's distal end (30) is touching a point at the squeeze parts (16) and transfers such a pinching power on them that they are forced together with a predetermined squeezing force. The angle (V3) between the squeeze parts (16), when the gripping points (19) touch each other, is preferably between 20 and 30 degrees at the same time as the angle (V4) between the gripping parts (18) is preferably between 10 and 15 degrees. As previously mentioned, the squeezing force between the gripping parts (18) and the gripping points (19) is preferably adjusted so that the grip on the tick's body (40) and head (38) will be released when attempts are made at pulling if the tick's head (38) has not loosened enough by turning the head (38) a sufficient number of times.

What is claimed is:

1. A tweezer for removal of ticks which have entered into skin, said tweezer comprising a pair of substantially flat spring like legs joined together at one end and having symmetrical gripping points at the opposite end thereof, said legs being symmetrical about the longitudinal axis of said tweezer and each having a first straight main part extending from said one end to form a second straight part acutely angled from said first straight main part at a first angle (VI) away from said longitudinal axis, said second straight part comprising a squeeze part which forms said first acute angle (VI) with said main part and which in turn merges with a third straight additional gripping part which forms a second acute angle (V2) with said gripping part and which at said opposite end is formed into said gripping point which is flat on the inside and obliquely angled on the outside and tapered into a double edged relatively thin knife-like point capable of reaching a tick head embedded in the skin, said symmetrical gripping points being usable as a knife to cut the skin around said embedded tick head while enabling easy visibility and access to said embedded tick head when disposed in a gripping position of said legs, said gripping points further being disposable in a ready position of said legs at a distance from a line which comprises an extension of said respective first straight main parts inside, said gripping points normally being spaced apart in said ready position after said straight main parts are brought together; said tweezer further comprising a coil spring and a movable cylinder means movable over said legs for moving said gripping points from said ready position to a grasping position of said tick head, said coil spring resiliently biasing said cylinder means distal end against said squeeze parts in said grasping position of said tick head for transferring a pinching power to said squeeze parts sufficient for forcing said squeeze parts together with a predetermined squeezing force sufficient to bias said normally spaced apart gripping points together to enable said gripping points to substantially touch each other in said grasping position of said tick head, said squeeze parts being at a third predetermined acute angle (V3) with respect to each other when said gripping points substantially touch each other in said grasping position of said tick head at the same time as said gripping parts are at a fourth predetermined angel (V4) with respect to each other, said predetermined squeezing force between said gripping parts and said gripping points being adjustable in said grasping position of said tick head and body so that the grip on the tick's body and head will be released when attempts are made at pulling if the tick's head has not loosened enough by turning the head a sufficient number of times.

2. A tweezer in accordance with claim 1 wherein said movable cylinder means is movable between a retracted position in which said gripping points are opened in said ready position and a released position in which said leg end portions and said gripping points are resiliently biased together in said grasping position for grasping the tick and its head with a predetermined force sufficient to cause said tweezer to lose its grip on the tick if the tick's head has not first been loosened by said turning of the head said sufficient number of times.

3. A tweezer in accordance with claim 2 wherein said turning of said head is brought about by turning said cylinder which maintains said predetermined pinching force by the help of said coil spring.

4. A tweezer in accordance with claim 1 wherein said turning of said head is brought about by turning said cylinder which maintains said predetermined pinching force by the help of said coil spring.

5. A tweezer in accordance with claim 1 wherein said angle (VI) is substantially in the range of 10-15 degrees.

6. A tweezer in accordance with claim 5 wherein said angle (V2) is substantially in the range of 25-35 degrees.

7. A tweezer in accordance with claim 6 wherein said angle (V3) is substantially in the range of 20-30 degrees.

8. A tweezer in accordance with claim 7 wherein said angle (V4) is substantially in the range of 10-15 degrees.

* * * * *